United States Patent [19]

Patel

[11] Patent Number: 4,786,491
[45] Date of Patent: Nov. 22, 1988

[54] SWEET EMULSION FOR CHEWING GUM

[75] Inventor: Mansukh M. Patel, Downers Grove, Ill.

[73] Assignee: Wm. Wrigley Jr. Company, Chicago, Ill.

[21] Appl. No.: 81,907

[22] Filed: Aug. 5, 1987

[51] Int. Cl.$^4$ .......... A61K 9/68; A23G 3/30; A23L 1/28

[52] U.S. Cl. .......... 424/48; 426/3; 426/5; 426/6; 426/103; 426/429; 426/548; 426/658

[58] Field of Search .......... 426/3, 5, 6, 103, 429, 426/548, 658; 424/48

[56] References Cited

U.S. PATENT DOCUMENTS

| | | |
|---|---|---|
| 2,929,723 | 3/1960 | Schultz et al. . |
| 4,122,205 | 10/1978 | Burge et al. . |
| 4,208,431 | 6/1980 | Friello et al. .......... 426/3 |
| 4,217,368 | 8/1980 | Witzel et al. .......... 426/3 |
| 4,228,198 | 10/1980 | Burge et al. . |
| 4,238,475 | 12/1980 | Witzel et al. .......... 426/3 |
| 4,241,091 | 12/1980 | Stroz et al. .......... 426/4 |
| 4,292,336 | 9/1981 | Latymer . |
| 4,301,178 | 11/1981 | Witzel et al. .......... 426/5 |
| 4,412,984 | 11/1983 | van der Loo et al. . |
| 4,452,820 | 6/1984 | D'Amelia et al. .......... 426/3 |
| 4,466,983 | 8/1984 | Cifrese et al. . |
| 4,493,849 | 1/1985 | Carroll et al. . |
| 4,525,363 | 6/1985 | D'Amelia et al. .......... 426/3 |
| 4,562,076 | 12/1985 | Arnold et al. . |
| 4,604,288 | 8/1986 | Glass et al. .......... 426/5 |
| 4,642,235 | 2/1987 | Reed et al. . |

FOREIGN PATENT DOCUMENTS

| | | | |
|---|---|---|---|
| 0185442 | 6/1986 | European Pat. Off. .......... 426/3 |
| 2850989 | 5/1979 | Japan .......... 426/3 |
| 1052249 | 3/1986 | Japan .......... 426/3 |
| 875763 | 8/1961 | United Kingdom .......... 426/3 |
| 2053651 | 2/1980 | United Kingdom .......... 426/3 |
| 2167641 | 6/1986 | United Kingdom .......... 426/3 |

Primary Examiner—John E. Kittle
Assistant Examiner—P. J. Ryan
Attorney, Agent, or Firm—Willian Brinks Olds Hofer Gilson & Lione Ltd.

[57] ABSTRACT

A method of adding a high intensity sweetener such as thaumatin, monellin and the like to chewing gum ingredients. The method comprises forming an emulsion comprising the high intensity sweetener, water, an emulsifier, and a hydrophobic ingredient which is preferably a flavor. Once formed, the emulsion is admixed with the chewing gum ingredients in any suitable manner.

34 Claims, No Drawings

SWEET EMULSION FOR CHEWING GUM

BACKGROUND OF THE INVENTION

The present invention relates to chewing gums having an improved release of thaumatin, monellin and like high intensity sweeteners and flavoring enhancers contained therein, and their method of manufacture.

In order to reduce carogenicity, many chewing gums employ sugar substitutes to provide sweetness and flavor. Sugar substitutes include high intensity sweeteners. High intensity sweeteners exhibit a greater sweetness than identical amounts of sucrose. High intensity sweeteners are known to be hundreds and sometimes thousands of times sweeter than sugar.

High intensity sweeteners of recent interest for use in gums include aspartame, acesulfame K, cyclamates, saccharin, sucralose, thaumatin, and monellin. Though most high intensity sweeteners currently known release relatively quickly from chewing gum, some, such as thaumatin, monellin, and the like, do not completely release from the chewing gum upon salivation or during chewing. As a result, the flavor and sweetness of these high intensity sweeteners is not fully experienced.

Thaumatin is a proteinaceous substance obtained from the fruit of the tropical plant Thaumatococcus daniellii which grows in tropical Africa. Thaumatin is about 2,000 to 3,000 times sweeter than sucrose and is known to have a lingering sweet aftertaste. The sweet protein monellin, obtained from the fruit of the tropical plant Diosocoreophyllum cumminsii, has taste properties similar to thaumatin.

Thaumatin and monellin, apart from their intense sweetness, are recognized as high-potency flavor and sweetness adjuvants capable of potentiating sweetness and flavor in chewing gum compositions. See, for example, van der Loo et al. U.S. Pat. No. 4,412,984 and Burge et al. U.S. Pat. No. 4,228,198.

Unfortunately, thaumatin and monellin are expensive and, when mixed directly with gum base and other ingredients in a conventional manner, must be present in substantial amounts before a noticeable flavoring or sweetness enhancement can be achieved. It is theorized that the thaumatin or monellin tend to become bound up in the gum base when mixed directly with the base, with the result that the base masks the flavor and sweetners potentiating effects of these sweet proteins.

Chewing gums, containing high intensity sweeteners with improved release characteristics would therefore constitute an advance in the art. These gums would be readily accepted and enjoy commercial success.

It is therefore an object of the present invention to provide chewing gums containing high intensity sweeteners having improved release characteristics. It is another object of the present invention to provide chewing gums which require less than the amount of high intensity sweetener currently believed in the art necessary to impart an acceptable sweetness and flavor. It is a further object of the present invention to provide a method of manufacturing chewing gums containing high intensity sweeteners having the release characteristics mentioned above. It is still yet another object of the present invention to provide a method of adding a high intensity sweetener to other chewing gum ingredients which is less hazardous and less sensitive to technician error.

These and other objects will become apparent in light of the following specification. It is to be understood, however, that the above mentioned objectives are not to be considered a limitation of the present invention, the scope of which is delineated in the appended claims.

SUMMARY OF THE INVENTION

In accordance with one embodiment of the present invention, there is provided a method of adding a high intensity sweetener such as thaumatin, monellin and the like to chewing gum ingredients. The method comprises forming an emulsion comprising the high intensity sweetener, water, an emulsifier, and a hydrophobic ingredient. Once formed, the emulsion is mixed with the chewing gum ingredients in a suitable manner. In accordance with another embodiment of the present invention, the hydrophobic ingredient comprises a flavor or a non-flavor such as vegetable oils.

In accordance with yet another embodiment of the present invention, there is provided a method of manufacturing a chewing gum comprising a high intensity sweetener and other chewing gum ingredients. The method comprises adding the high intensity sweetener to the other chewing gum ingredients in the form of an emulsion. The emulsion is formed by first dissolving the high intensity sweetener in water to obtain a aqueous high intensity sweetener solution. A second solution comprising an emulsifier in a hydrophobic ingredient is prepared by dissolving the appropriate amounts of emulsifier in the hydrophobic ingredient. The aqueous high intensity sweetener solution is then admixed with the emulsifier solution in an amount sufficient to form the emulsion.

In accordance with a further embodiment of the present invention, the use of thaumatin as the high intensity sweetener and lecithin as the emulsifier is contemplated in the manufacture of chewing gum.

In accordance with another embodiment of the present invention, a high intensity sweetener may be added to other confectionary ingredients in the form of an emulsion as described above. Accordingly, candies, bakery products, sauces, and the like are contemplated.

DETAILED DESCRIPTION OF PREFERRED EMBODIMENTS

It has now been discovered that when high intensity sweeteners of the type contemplated by the present invention are added to chewing gum ingredients in the form of an emulsion, flavor and sweetness are enhanced. When added in conventional manners, these high intensity sweeteners do not release the expected amount of sweetness and flavor during chewing. However, when added in accordance with the method of the present invention, sweetness may be enhanced up to ten times that achieved by addition through conventional methods. Such an increase in flavor and sweetness provides significant economic savings since, for example, only one-tenth the amount of high intensity sweetener previously thought required need be used.

Another advantage of the present invention is that the loss of high intensity sweetener from manufacturing personnel handling may be substantially reduced. Since the sweeteners contemplated by the present invention may be very intense, at least 300 to 3000 more times than that of sucrose, very little is required to achieve an acceptable level of sweetness and flavor. Accordingly, a small error in the amount of high intensity sweetener added can cause significant variations in product quality. When the sweetener is added in the form of an emulsion, however, such wide product sweetness and flavor variations may be substantially reduced or even eliminated.

A still further advantage of the present invention is that the loss of thaumatin to the atmosphere while being handled is reduced. Thaumatin is available as a very fine powder and when handled significant quantities often become suspended in the atmosphere creating an unsafe environment. Manufacturing personnel may be sensitive to the fine particles in the atmosphere and may react adversely. According to the present invention, adding thaumatin to other chewing gum ingredients while in an emulsion reduces this hazard.

These and other advantages will become apparent to those skilled in the art in light of the following disclosure. It is to be understood, however, that the present invention is not intended to be limited by the advantages discussed or contemplated. It is the appended claims and their equivalents which define the scope of the invention.

In accordance with the present invention, the high intensity sweeteners contemplated are added in the form of an emulsion. The emulsion may be formed in any way. In accordance with one embodiment, the emulsion is prepared by first dissolving the high intensity sweetener in water to form an aqueous solution, and then emulsifying the aqueous solution with a compound possessing hydrophobic characteristics. The aqueous solution may be emulsified with the hydrophobic compound in any known manner, but it is preferred that an emulsifier be employed to accomplish this purpose.

The emulsion contemplated by the present invention comprises about 0.008 to about 16 percent by weight high intensity sweetener and specifically about 0.008 to about 16 percent by weight thaumatin, monellin or a combination thereof; about 6 to about 65 percent by weight water; about 0.2 to about 10 percent by weight emulsifier; and about 19 to about 85 percent by weight of a hydrophobic ingredient.

Preferably, the hydrophobic compound of the present invention comprises a liquid flavor oil. Such flavor oils include synthetic and natural flavoring compounds. Th hydrophobic compound of the present invention may also comprise non-flavor compounds. Thus, vegetable oils and other hydrophobic non-flavor compounds are also contemplated.

In accordance with another embodiment of the present invention, the aqueous sweetener solution may comprise up to 25 weight percent of the high intensity sweetener. Concentrations above 25 weight percent, however, should be avoided to prevent foaming of the solution. Preferably, the aqueous sweetener solution comprises about 1 weight percent of the sweetener. In any event, the present invention contemplates aqueous solutions of various concentrations.

In accordance with another embodiment of the present invention, the aqueous solution may be heated in order to enhance dissolution and/or its emulsifying action. In addition, glycerin, or a similar compound, may be added to the aqueous solution to prevent gellation.

High intensity sweeteners contemplated include thaumatin, monellin, and other high intensity sweeteners having similar release characteristics during chewing. Accordingly the present invention contemplates high intensity sweeteners having a low release when mixed directly with other ingredients. Though a precise method for determining the release characteristics of thaumatin and monellin is not presently known, it is believed that the high intensity sweeteners contemplated have less than about 20% by weight release from a gum after about ten minutes of chewing when admixed directly in their normal form. As used herein, the term "normal form" is intended to mean the form in which the sweetener is normally added to a chewing gum ingredient(s). The form may thus be liquid or powder, but most likely will be powder.

Preferably, thaumatin, monellin, and like high intensity sweeteners are contemplated. It is to be understood, however, that other sweeteners not specifically mentioned herein may also be employed in the present invention. Furthermore, any combination of these high intensity sweeteners may also be employed.

The emulsion of the present invention may be prepared by mixing the aqueous solution with flavor. The emulsion may be formed by any manner known in the art, but preferably the emulsion is formed with the aid of an emulsifier.

Emulsifiers contemplated by the present invention include any span, tween, or similar compound. Preferably, the emulsifier employed is matched to the hydrophobic compound by its Hydrophile-Lipophile Balance (HLB) number. The HLB of an emulsifier is an expression of its hydrophiliclipophile balance, i.e., the balance of the size and strength of the hydrophilic and the lipophilic groups of an emulsifier. The HLB system which has been known to those skilled in the art since the late 1940's is useful in choosing an appropriate emulsifier. If a flavor is employed, a most preferable emulsifier is lecithin, a well known, inexpensive emulsifier.

It is further contemplated by the present invention that the emulsion may also comprise other ingredients nonessential to the formation of the emulsion. Such ingredients include but are not limited to coloring agents such as dyes, lakes, and natural colorants, food acids, inorganic salts, glycerin and like components, medicants, and relatively fast releasing high potency sweeteners such as aspartame, sucralose, acesulfame-K, cyclamates, and saccharin.

Flavors contemplated by the present invention include any liquid flavoring which is of food acceptable quality. The flavor may comprise essential oils, synthetic flavors, or mixtures thereof including but not limited to oils derived from plants and fruits such as citrus oils, fruit essences, peppermint oil, spearmint oil, clove oil, oil of wintergreen, anise, and the like. Artificial flavoring components are also contemplated by the present invention. Those skilled in the art will recognize that natural and artificial flavors may be combined in any sensorally acceptable blend. All such flavors and blends are contemplated by the present invention.

In accordance with one embodiment of the present invention, the emulsifier is first dissolved in a flavor prior to admixture with an aqueous sweetener solution. The emulsifier may be dissolved in any acceptable amount, which depends upon the particular combination of emulsifier and flavor selected. For example, when lecithin is employed as an emulsifier, it may be dissolved in flavor to yield a solution containing as much as 11 weight percent lecithin. A lecithin in flavor solution containing about 2 weight percent or less lecithin, however, is preferred.

The aqueous solution sweetener solution and the flavor solution may be combined in any acceptable ratio, which will depend upon the solution concentrations and the amount of sweetener and flavor desired in the chewing gum product. In general, ratios of about 1:10 to about 3:1 are contemplated. It is to be understood, however, that the ratios can differ greatly, and are not to be considered a limitation of the present invention.

For example, in the case of a thaumatin sweetener, a lecithin emulsifier, and a flavor, the preferred ratio of aqueous thaumatin solution to lecithin in flavor solution is about 1:1 when a 1 weight percent thaumatin solution and a 1 weight percent lecithin in flavor solution are admixed.

Additional ingredients such as those mentioned below may also be present in the chewing gum. These ingredients include other flavor and sweetness modifiers, texture modifiers, colors, and similar ingredients known to those skilled in the art. It is to be understood, however, that the present invention is not limited by such additional ingredients.

The present invention may also be utilized in the manufacture of any confectionary item. Thus items such as sugar and sugarless gum products, bakery products, and sauces are also contemplated. Preferably, however, the present invention is utilized in the manufacture of chewing gums.

In general, a chewing gum composition comprises a water soluble bulk portion and a water insoluble chewable gum base portion and, typically water insoluble flavors. The water soluble portion dissipates with a portion of the flavor over a period of time during chewing. The gum base portion is retained in the mouth throughout the chew.

The insoluble gum base generally comprises elastomers, resins, fats and oils, waxes, softeners and inorganic fillers. Elastomers may include polyisobutylene, isobuylene-isoprene copolymer, styrene butadiene rubber as well as natural latexes such as chicle. Resins include polyvinylacetate and terpene resins. Fats and oils may also be included in the gum base, including tallow, hydrogenated and partially hydrogenated vegetable oils, and cocoa butter. Commonly employed waxes include paraffin, microcrystalline and natural waxes such as beeswax and carnuba. The insoluble gum base constitutes between about 5 to 95 weight percent of the gum. Preferably the insoluble gum base comprises about 10 to about 50 weight percent of the gum and more preferably about 20 to about 30 weight percent.

The gum base typically also includes a filler component. The filler component such as calcium carbonate, magnesium carbonate, talc, dicalcium phosphate and the like. The filler may constitute between about 5 to about 60 weight percent of the gum base. Preferably, the filler comprises about 5 to 50 weight percent of the chewing gum base.

Gum bases typically also contain softeners, including glycerol monostearate and glycerol triacetate. Further, gum bases may also contain optional ingredients such as antioxidants, colors, and emulsifiers. The present invention contemplates employing any commercially acceptable gum base.

The water soluble portion of chewing gum may further comprise softeners, sweeteners, flavors and combinations thereof. Softeners are added to the chewing gum in order to optimize the chewability and mouth feel of the gum. Softeners, also known in the art as plasticizers or plasticizing agents, generally constitute between about 0.5 to about 15.0 weight percent of the chewing gum. Softeners contemplated by the present invention include glycerin, lecithin, and combinations thereof. Further, aqueous sweetener solutions such as those containing sorbitol, hydrogenated starch hydrolysates, corn syrup and combinations thereof may be used as softeners and binding agents in gum.

In addition to the high intensity sweeteners contained in the emulsion already mentioned, other sweeteners are also contemplated by the present invention for direct addition to the chewing gum. These sweeteners include both sugar and sugarless components. Sugar sweeteners generally include saccharide containing components commonly known in the chewing gum art which comprise but are not limited to sucrose, dextrose, maltose, dextrin, dried invert sugar, fructose, levulose, galactose, corn syrup solids, and the like, alone or in any combination. Sugarless sweeteners include components with sweetening characteristics but are devoid of the commonly known sugars and comprise but are not limited to sugar alcohols such as sorbitol, mannitol, xylitol, hydrogenated starch hydrolysates, maltitol, and the like, alone or in any combination. Also contemplated for direct addition to the gum are relatively faster releasing gums such as aspartame, sucralose, acesulfame-K, cyclamates and saccharin.

Those skilled in the art will recognize that any combination of sugar and/or sugarless sweeteners may be employed in the chewing gum. Further, those skilled in the art will recognize the sweetener may be present in the chewing gum in whole or in part as a water soluble bulking agent. In addition, the softener may be combined with the sweetener such as in an aqueous sweetener solution.

A flavor may be present in the chewing gum in an amount within the range of from about 0.1 to about 10.0 weight percent and preferably from about 0.5 to about 3.0 weight percent of the gum. The flavor may comprise the components already mentioned.

Optional ingredients such as colors, emulsifiers and pharmaceutical agents may be added to the chewing gum.

In general, chewing gum is manufactured by sequentially adding the various chewing gum ingredients to any commercially available mixer known in the art. After the ingredients have been thoroughly mixed, the gum mass is discharged from the mixer and shaped into the desired form such as by rolling into sheets and cutting into sticks, extruding into chunks, or casting into pellets.

Generally, the ingredients are mixed by first melting the gum base and adding it to the running mixer. The base may also be melted in the mixer itself. Color may also be added at this time. A softener such as glycerin may then be added next along with syrup and a portion of bulking agent. Further portions of the bulking agent may then be subsequently added to the mixer.

A flavor is typically added with the final portion of the bulking agent. In accordance with the present invention, the emulsion which may contain all or a portion of the flavor is preferably added at this time to minimize the volatilization of flavor. It is to be understood, however, that under proper conditions, the emulsion of the present invention may be added at any time during the gum manufacturing process.

The emulsion of the present invention may be added at any time during the mixing procedure. Preferably, when the emulsion comprises flavor, the emulsion is added at such a time as to minimize flavor volatilization, and most preferably in the later part of the mixing procedure. When the emulsion comprises a non-flavor hydrophobic compound, volatilization is not a major concern and thus the emulsion may be admixed at any time.

The entire mixing procedure typically takes from five to fifteen minutes, but longer mixing times may sometimes be required. Those skilled in the art will recognize that many variations of the above described procedure may be followed.

It is to be understood that an equivalent range of changes and modifications to the preferred embodiments described above are also contemplated by the present invention. The following examples are not to be construed as a limitation upon the present invention, but are included merely as an illustration of various embodiments.

EXAMPLE I

An aqueous solution containing 10 weight percent thaumatin was prepared by dissolving 10 parts thaumatin into 90 parts water. The solution was agitated to ensure complete dissolution and set aside.

A 1 weight percent lecithin in flavor solution was prepared by dissolving 1 part lecithin in 99 parts of peppermint flavor. The lecithin, known as Centrolex R, was obtained from Central Soya. The lecithin in flavor solution was vigorously agitated to ensure complete dispersion of the lecithin into the flavor.

The aqueous thaumatin solution was then admixed with the lecithin in flavor solution at a 1:10 ratio. The mixture was vigorously agitated until an emulsion was obtained.

A 1000 gram batch of chewing gum was prepared by admixing a gum base, bulking agent, softener, and 5.5 grams of the emulsion. The emulsion was added near the end of the mixing process. The resulting formulation contained 50 ppm thaumatin and 0.495 wt. % peppermint flavor.

Chewing tests of the gum showed that about 50 ppm of thaumatin in gum, when added in emulsion form, yielded a flavor and sweetness equivalent to about 100 ppm in gum when added as a water solution.

Additional similar tests showed that the advantage of adding thaumatin in the emulsion form over adding it in the powdered form to a chewing gum is even greater. In this instance, 10–50 ppm was found to be equivalent to about 100–500 ppm.

EXAMPLE II

An aqueous solution containing 1 weight percent thaumatin, 1 weight percent aspartame and 98 weight percent water was prepared by dissolving one part aspartame and one part thaumatin into 98 parts water. The solution was agitated to ensure complete dissolution and set aside.

An emulsifier in flavor solution was prepared by dissolving two parts lecithin (Centrolex R from Central Soya) in 98 parts of spearmint flavor. The emulsifier in flavor solution was vigorously agitated to ensure complete dissolution of the emulsifier into the flavor.

The aqueous sweetener solution was then admixed with the emulsifier in flavor solution at a 1:1 ratio. The admixture was vigorously agitated until an emulsion was obtained.

A chewing gum was prepared by admixing a gum base, bulking agent, softener, and the emulsion according to the formulation of TABLE I. The chewing gum contained about 56 ppm aspartame, 56 ppm thaumatin, and 0.55 weight percent flavor in lecithin.

TABLE I

| Ingredient | Weight Percent |
| --- | --- |
| Base | 20.68 |
| Sugar | 49.79 |
| Corn Syrup | 16.86 |
| Dextrose Monohydrate | 10.55 |
| Glycerin (4% $H_2O$) | 0.94 |
| Color | 0.06 |
| Emulsion | 1.12 |
|  | 100.00 |

The present example illustrates that other high intensity sweeteners which possess relatively faster release characteristics than thaumatin during chewing may also be added to the chewing gum ingredients as an emulsion.

I claim:

1. A method of adding thaumatin to chewing gum ingredients, said method comprising:
    (a) forming an emulsion comprising about 0.008 to about 16 percent by weight thaumatin, about 6 to about 65 percent by weight water, about 0.2 to about 10 percent by weight emulsifier, and about 19 to about 85 percent by weight of a hydrophobic ingredient; and
    (b) admixing said emulsion with said chewing gum ingredients.

2. The method of claim 1 wherein said hydrophobic ingredient is a flavor.

3. The method of claim 1 wherein said hydrophobic ingredient comprises vegetable oils.

4. The method of claim 1 wherein said emulsifier comprises lecithin.

5. A method of adding monellin to chewing gum ingredients, said method comprising:
    (a) forming an emulsion comprising about 0.008 to about 16 percent by weight monellin, about 6 to about 65 percent by weight water, about 0.2 to about 10 percent by weight emulsifier, and about 19 to about 85 percent by weight of a hydrophobic ingredient; and
    (b) admixing said emulsion with said chewing gum ingredients.

6. The method of claim 5 wherein said hydrophobic ingredient is a flavor.

7. The method of claim 5 wherein said hydrophobic ingredient comprises vegetable oils.

8. The method of claim 5 wherein said emulsifier comprises lecithin.

9. A method of manufacturing a chewing gum comprising thaumatin and other chewing gum ingredients, said method comprising the steps of:
    (a) dissolving said thaumatin in water to obtain an aqueous thaumatin solution comprising about 0.1 to about 25 percent by weight thaumatin;
    (b) dissolving an emulsifier in a hydrophobic compound to obtain an emulsifier solution comprising about 0.1 to about 11 percent by weight emulsifier;
    (c) mixing the aqueous thaumatin solution with the emulsifier solution in a ratio about 1:10 to about 3:1 to form an emulsion; and
    (d) adding said emulsion to said chewing gum ingredients to obtain said chewing gum.

10. The method of claim 9 wherein said emulsifier solution comprises about 0.5 to about 5 percent by weight emulsifier.

11. The method of claim 9 wherein said emulsifier comprises lecithin.

12. The method of claim 9 wherein said thaumatin solution further comprises glycerin.

13. The method of claim 9 further comprising heating said thaumatin solution prior to mixing with said emulsifier solution.

14. The method of claim 9 wherein said thaumatin solution comprises about 1 percent by weight thaumatin.

15. The method of claim 9 wherein said hydrophobic compound comprises peppermint, spearmint, clove, wintergreen, or combinations thereof.

16. The method of claim 15 wherein said emulsifier solution comprises about 2 percent by weight emulsifier.

17. The method of claim 9 wherein said thaumatin solution and said emulsifier solution are mixed at a weight ratio of about 1:1.

18. The method of claim 9 wherein said chewing gum comprises a bulking agent ingredient.

19. The method of claim 9 wherein said chewing gum comprises a softener ingredient.

20. The method of claim 9 wherein said emulsifier comprises a span, a tween or combinations thereof.

21. A method of manufacturing a chewing gum comprising monellin and other chewing gum ingredients, said method comprising the steps of:
   (a) dissolving said monellin in water to obtain an aqueous monellin solution comprising about 0.1 to about 25 percent by weight monellin;
   (b) dissolving an emulsifier in a hydrophobic compound to obtain an emulsifier solution comprising about 0.1 to about 11 percent by weight emulsifier;
   (c) mixing the aqueous monellin solution with the emulsifier solution in a ratio of about 1:10 to about 3:1 to form an emulsion; and
   (d) adding said emulsion to said chewing gum ingredients to obtain said chewing gum.

22. The method of claim 21 wherein said emulsifier solution comprises about 0.5 to about 5 percent by weight emulsifier.

23. The method of claim 21 wherein said emulsifier comprises lecithin.

24. The method of claim 21 wherein said monellin solution further comprises glycerin.

25. The method of claim 21 further comprising heating said monellin solution prior to mixing with said emulsifier solution.

26. The method of claim 21 wherein said monellin solution comprises about 1 percent by weight monellin.

27. The method of claim 21 wherein said hydrophobic compound comprises peppermint, spearmint, clove, wintergreen, or combinations thereof.

28. The method of claim 27 wherein said emulsifier solution comprises about 2 percent by weight emulsifier.

29. The method of claim 21 wherein said monellin solution and said emulsifier solution are mixed at a weight ratio of about 1:1.

30. The method of claim 21 wherein said chewing gum comprises a bulking agent ingredient.

31. The method of claim 21 wherein said chewing gum comprises a softener ingredient.

32. The method of claim 21 wherein said emulsifier comprises a span, a tween or a mixture thereof.

33. A method of adding a high intensity sweetener having a low release during chewing when added directly in its normal form to chewing gum ingredients, said mehod comprising:
   (a) forming an emulsion comprising about 0.008 to about 16 percent by weight high intensity sweetener, about 6 to about 65 percent by weight water, about 0.2 to about 10 percent by weight emulsifier, and about 19 to about 85 percent by weight of a hydrophobic ingredient; and
   (b) admixing said emulsion with said chewing gum ingredients.

34. The method of claim 33 wherein said high intensity sweetener has less than about 20% by weight release after about ten minutes of chewing when added in its powder form.

* * * * *

UNITED STATES PATENT AND TRADEMARK OFFICE
CERTIFICATE OF CORRECTION

PATENT NO. : 4,786,491
DATED : November 22, 1988
INVENTOR(S) : Mansukh M. Patel

Page 1 of 2

It is certified that error appears in the above-identified patent and that said Letters Patent is hereby corrected as shown below:

IN THE SUMMARY OF THE INVENTION

In column 2, line 25, please delete "a" and substitute therefor --an--.

IN THE DETAILED DESCRIPTION
OF PREFERRED EMBODIMENTS

In column 3, line 43, please delete "Th" and substitute therefor --The--.

In column 5, line 41, please delete "lnclude" and substitute therefor --include--.

UNITED STATES PATENT AND TRADEMARK OFFICE
CERTIFICATE OF CORRECTION

PATENT NO. : 4,786,491

DATED : November 22, 1988

INVENTOR(S) : Mansukh M. Patel

It is certified that error appears in the above-identified patent and that said Letters Patent is hereby corrected as shown below:

<u>IN THE CLAIMS</u>

In column 10, line 31, please delete "mehod" and substitute therefor --method--.

Signed and Sealed this

Sixth Day of August, 1991

*Attest:*

HARRY F. MANBECK, JR.

*Attesting Officer*     *Commissioner of Patents and Trademarks*